(12) United States Patent
De Stasio et al.

(10) Patent No.: US 6,770,020 B2
(45) Date of Patent: Aug. 3, 2004

(54) METHOD OF USING GADOLINIUM NEUTRON CAPTURE TO TREAT CANCERS

(75) Inventors: Gelsomina De Stasio, Madison, WI (US); Benjamin Gilbert, Berkeley, CA (US); Bradley H. Frazer, Madison, WI (US); Roberto Pallini, Rome (IT); Luigi Maria Larocca, Rome (IT); Delio Mercanti, Rome (IT); Patrizia Casalbore, Rome (IT)

(73) Assignee: Wisconsin Alumni Research Foundation, Madison, WI (US)

( * ) Notice: Subject to any disclaimer, the term of this patent is extended or adjusted under 35 U.S.C. 154(b) by 35 days.

(21) Appl. No.: 10/135,069

(22) Filed: Apr. 30, 2002

(65) Prior Publication Data

US 2003/0049202 A1 Mar. 13, 2003

Related U.S. Application Data

(60) Provisional application No. 60/287,966, filed on May 1, 2001.

(51) Int. Cl.[7] .................................................. A61N 5/00
(52) U.S. Cl. ............................ 600/3; 600/1; 250/251; 424/1.65; 424/9.3; 424/9.36; 424/9.361; 424/9.362; 424/617; 514/184; 514/492
(58) Field of Search ......................... 600/1, 3; 250/251; 424/1.65, 9.3, 9.36, 9.361, 9.362, 617; 514/184, 492

(56) References Cited

U.S. PATENT DOCUMENTS 5,888,997 A    3/1999 Sessler et al.

OTHER PUBLICATIONS

Ausserer et al. (1989) *Anal. Chem.* 61, 2690–2695.
Berger et al., (1997) in *Progress in Neutron Capture Therapy*, eds. Larsson, B., Crawford, J., & Weinrich, R. (Elsevier, Amsterdam), 440–446.
Chadha et al., (1998). *Int. J. Radiation Oncology, Biol. Phys.* 40, 829–834.
De Stasio et al., (1993) *Neuroreport* 4, 1175–8.
De Stasio et al., (1999) *Anal. Biochem.* 266, 174–180.
De Stasio et al., (1999) *Rev. Sci. Instrum.* 70, 1740–1742.
Gilbert et al., *Phys. Rev. E.* in press. (1999).
Gilbert et al., (2000) *Frontiers in Bioscience* 5, 10–17.
Hatanaka et al, (1994) *Int. J. Radiation Oncology, Biol. Phys.* 28, 1061–1066.
Hill et al., (1995) *Proc. Natl. Acad. Sci.* 92, 12126–12130.
Hofmann et al., (1999) *Invest. Radiol.* 34, 126–133.
Kasrai et al. (1996) *Appl. Surf. Sci.* 99, 303–309.
Kleihues et al., (1993) *Brain Pathol.* 3, 255–268.
Laster et al., (1996) *Acta Oncol.* 35, 917–923.
Li et al. (1999) *J. Am. Chem. Soc.* 121:1413–1414.
Martin et al., (1989) *Pigment Cell Res.* 2, 330–332.
Nakanishi et al., (1999) *Proc. Natl. Acad. Sci.* 96, 238–241.
Niendorf t al., (1986) *Acta Radiol. Suppl.* 369, 561–563.
Pak t al., (1995) *Proc. Natl. Acad. Sci.* 92, 6986–6990.
Rivard et al., (1997) in *Progress in Neutron Capture Therapy for Cancer*, eds. Larsson, B., Crawford, J., & Weinrich, R. (Elsevier, Amsterdam), 430–435.
Sauerwein et al., (1999) *Strahlentharapie und Onkologie* 175, 108–111.
Shih et al., (1992).in *Progress in Neutron Capture Therapy*, eds. Allen, B. J., Moore, D. E., & Harrington, B. V. (Plenum Press, New York), 183–186.
Shih et al., (1992) *Med. Phys.* 19, 733–744.
Weinmann et al., (1984) *Am. J. Roentgenol.* 142, 619–624.
Yoshida et al., (1989) *Mag. Reson. Imaging* 7, 9–15.
Young et al., (1996) *Proc. Natl. Acad. Sci.* 93, 6610–6615.

*Primary Examiner*—Frederick Krass
(74) *Attorney, Agent, or Firm*—Joseph T. Leone, Esq.; DeWitt Ross & Stevens S.C.

(57) ABSTRACT

Described is a method of using gadolinium-containing compounds as agents for neutron capture therapy to treat neoplastic cell growth. The subject is exposed to a gadolinium-containing compound for a time sufficient to allow the compound to accumulate in neoplastic cells. The subject is then exposed to a thermal and/or epithermal neutron flux, thereby initiating a neutron capture reaction in the gadolinium atoms that results in specific death of neoplastic cells.

23 Claims, 5 Drawing Sheets

METHOD OF USING GADOLINIUM NEUTRON CAPTURE TO TREAT CANCERS

PRIORITY

Priority is hereby claimed to provisional patent application Ser. No. 60/287,966, filed May 1, 2001, the contents of which are incorporated herein by reference.

FIELD OF THE INVENTION

The invention is directed to a method to inhibit the growth of cancer cells by contacting the cells (either in vitro or in vivo) with a gadolinium-containing agent to increase specifically the neutron capture cross-section within the nuclei of the cancerous cells. Upon exposure to a neutron flux, the cancer cells containing the gadolinium-containing agents are specifically destroyed or their growth is inhibited.

BIBLIOGRAPHIC CITATIONS

Complete bibliographic citations to the references discussed herein are contained in the Bibliography section, immediately preceding the Claims.

DESCRIPTION OF THE RELATED ART

Modern medical research often benefits from collaborations between physicists and medical doctors. Magnetic resonance imaging, computerized axial tomography, and laser surgery are only a few offshoots of such teamwork, demonstrating that an interdisciplinary view of medicine has become essential. Now-rampant medical conditions such as cardiovascular disease, dementia, and cancer, are actively being explored by a diversity of scientists. In this same vein of interdisciplinary investigation, the present application discloses a new therapy for treating cancers (i.e., neoplastic growths) in general, and, in the preferred embodiment of the invention, malignant brain cancers.

Neutron Capture Therapy (NCT) is a non-invasive, experimental therapy that has been proposed in the past to treat malignant gliomas. The conventional therapy is based on a binary approach: In the first step, the patient is intravenously injected with an NCT-enhancing agent; that is, a tumor-seeking compound containing an isotope that has a capture cross section for thermal neutrons many times greater than any other elements present in the surrounding tissue. In the second step, the patient's skull is exposed to thermal neutrons. A portion of the thermal neutrons are captured by the NCT-enhancing agent, thereby inducing in the NCT agent a localized, biologically-destructive nuclear reaction.

An NCT agent that has been extensively investigated is the isotope boron-10 ($^{10}$B), which undergoes the reaction $^{10}$B(n,α)$^{7}$Li. When $^{10}$B is present in tissue irradiated by a neutron flux, almost all of the radiation dose delivered to the individual cells results from the high linear energy transfer ("LET," i.e., stopping power) fission products of the boron neutron capture reaction. For many years, the greatest challenge for NCT using boron-containing sensitizers has been to link the $^{10}$B isotope to a tumor-seeking compound, thereby adding greater specificity to the radiation dose. In short, absent specificity for tumor cells, NCT is no more efficacious than conventional radio-therapies, i.e, non-specific radiation treatments that deliver the radiation dose equally to malignant and non-malignant cells alike. The key to unlocking the potential of NCT is to deliver a radiotoxic dose only to tumor cells, thereby sparing the surrounding healthy tissue from radiation-induced damage.

The discovery of two boronated compounds that exhibited tumor-selective uptake has resulted in clinical trials of Boron Neutron Capture Therapy (BNCT). These trials are currently underway in Europe, Japan, and the United States.[1][2][3] The uptake mechanisms of these compounds into tumor cells are thought to be different, and a major effort is being put into the synthesis of novel compounds for BNCT utilizing alternative cancer targeting strategies.[4][5][6]

To date, however, the full potential of NCT as a means to treat cancers remains largely unrealized. There remains a long-felt and unsatisfied need for biologically well-tolerated compounds that simultaneously exhibit very high neutron capture cross-sections, high levels of tumor-specific uptake, and high levels of tumor cell-specific kill or growth inhibition. The present invention addresses this long-felt need.

SUMMARY OF THE INVENTION

Compounds containing gadolinium 155 ($^{155}$Gd) and/or gadolinium-157 ($^{157}$Gd) are a powerful alternative NCT isotope as compared to $^{10}$B. Gd neutron capture therapy, designated herein as "GdNCT," has never been clinically tested.[7][8][9] The present inventors have determined, however that certain Gd-containing compounds are excellent neutron capture agents for several reasons, including the following:

$^{157}$Gd, which is found with a natural abundance of 15.7%, is the most effective isotope in terms of neutron capture cross-section, having the largest thermal neutron cross-section (254,000 barn) of all stable isotopes currently known. For sake of comparison, $^{10}$B has a neutron capture cross-section of 3,840 barn, $^{16}$O=0.00019 barn, $^{12}$C=0.0035 barn, $^{1}$H=0.333 barn, and $^{14}$N=1.83 barn.

Some gadolinium compounds are known to accumulate in brain tumors and not in the surrounding healthy tissue. Some of these compounds currently are used as tumor contrast-enhancing agents for magnetic resonance imaging (MRI) due to the large magnetic moment of the $Gd^{3+}$ ion.[11]

While the $Gd^{3+}$ ion is itself toxic, its usefulness in MRI stimulated the search for compounds such as the Gd-DTPA complex described herein, which is both stable in the blood stream and non-toxic. The pharmacokinetics, biodistribution and tolerance of Gd-DTPA and other Gd-containing compounds used as MRI contrast agents are well documented.[12][13]

The gadolinium neutron capture reaction, $^{157}$Gd(n,γ) $^{158}$Gd, provokes complicated nuclear decay transitions that generate prompt γ emission up to 7.8 MeV, accompanied by the emission of internal conversion electrons, mostly Auger electrons in the energy range of about 41 keV and below. Both γ rays and Auger electrons are low LET radiation, with contrasting ranges and biological effects in tissue. Gamma rays travel through the whole thickness of the tissue, and are weakly absorbed by both healthy and tumor tissues. Hence these capture products would deliver dose widely, independent of the precise location of a GdNCT agent in the tumor cells.

By contrast, Auger electrons, which are mass and charge-carrying, are highly ionizing over a short range. The longest radiation length is on the order of tens of nanometers for the most energetic electrons. Most favorably for GdNCT, Auger electrons appear to induce double-stranded DNA damage when the Gd is sufficiently close to the DNA.[14] Consequently, the dose enhancement due to the electrons emitted in the GdNCT reaction would be most substantial when the electrons originate from a site within the cell nucleus, i.e. when the Gd-containing NCT agent accumulates in the cell nuclei. Studies in the literature demonstrate that GdNCT can be used to kill tumor cells,[15][16] but do not differentiate the relative efficacies of the γ rays and Auger electrons. It is often assumed that gadolinium diethylene triamine pentaacetic acid (Gd-DTPA, a gadolinium-containing compound that is used as an MRI contrast agent), does not penetrate the plasma membrane, but no experiment has been performed to tackle the issue of Gd-DTPA penetration (or other gadolinium-containing compounds) into tumor cells.

In the Examples that follow, human glioblastoma cells were exposed to the gadolinium-containing compound Gd-DTPA and then observed to determine whether the gadolinium accumulated intracellularly and/or intranuclearly. Three independent techniques were used to show cellular uptake of the compounds by cultures of tumor cells. One of these methods (inductively-coupled plasma mass spectrometry, ICP-MS) is a bulk analysis method, the other two methods (x-ray spectromicroscopy and Time of Flight Secondary Ion Mass Spectrometry, TOF-SIMS) are microchemical surface analytical methods. Spectromicroscopy is a well-established technique in materials science, but is only rarely used for the microchemical analysis of physiological and trace elements in biological specimens.[17][18] As described herein, synchrotron spectromicroscopy was used to observe directly the intracellular distribution of gadolinium, via x-ray absorption spectroscopy at the Gd 3d edge. It was demonstrated that Gd-DTPA penetrates both the outer and nuclear membranes, and additionally shows preferential accumulation in the cell nuclei. This result has been confirmed by TOF-SIMS analysis.

Thus, the invention is directed to a method of selectively inhibiting the growth of neoplastic cells. The method comprises first contacting neoplastic cells (in vitro or in vivo) with a Gd-containing compound for a time sufficient to allow the Gd-containing compound to be internalized within nuclei of the neoplastic cells. The neoplastic cells are then exposed to a neutron flux of thermal and/or epithermal neutrons sufficient to induce a neutron capture reaction in Gd atoms within the Gd-containing compound internalized by the neoplastic cells. Growth of the neoplastic cells is thus inhibited due to cellular damage caused by Auger electrons and gamma radiation emitted by Gd atoms that underwent the neutron capture reaction.

The preferred embodiment of the invention is a method of treating glioma in mammalian subjects, especially humans, using the above-described GdNCT reaction. In the preferred embodiment, an amount of a non-toxic, Gd-containing compound (the amount being sufficient to allow the compound to be internalized within nuclei of glioma cells within the subject) is administered to a subject suffering from glioma. The subject is then exposed to a thermal and/or epithermal neutron flux sufficient to induce a neutron capture reaction in Gd atoms within the Gd-containing compound internalized by the glioma cells. Growth of the glioma cells is thereby inhibited (or the cells are killed outright) due to cellular damage caused by the Auger electrons and gamma radiation emitted by Gd atoms that underwent the neutron capture reaction.

DETAILED DESCRIPTION OF THE INVENTION

Gd is a potential agent for neutron capture cancer therapy (GdNCT). The microdistribution of gadolinium was observed in cultured human glioblastoma cells exposed to gadolinium diethylene triamine pentaacetic acid (Gd-DTPA). With three independent techniques, it was demonstrated that this compound penetrates the plasma membrane and the nuclear membrane, but has no effect on cell survival (none was observed). A systematic micro-chemical analysis revealed a higher Gd accumulation in cell nuclei compared to cytoplasm. This is significant for prospective GdNCT because the proximity of Gd to DNA increases the cell-killing potential of the short-range Auger electrons emitted during the neutron capture reaction.

Thermal and Epithermal Neutron Flux:

As defined herein, "thermal neutrons" are neutrons having an energy equal to or less than about 0.5 eV. A thermal neutron flux for use in the present invention can be generated by any means now known in the art or developed in the future for generating a steady stream of thermal neutrons that can be directed to impinge upon a desired target. In short, the source of the thermal neutrons is not critical to the function of the invention, so long as the neutron source generates a steady, controllable stream of neutrons having an energy equal to or less than about 0.5 eV.

As defined herein, "epithermal neutrons" are neutrons having an energy equal to or less than about 10,000 eV and greater than about 0.5 eV.

Conventional sources of thermal and epithermal neutrons include nuclear reactors and large particle accelerators. In nuclear reactors, a fissionable material, such as $^{235}U$, undergoes a fission reaction to yield a flux of fast neutrons, which then pass through a moderating material to yield thermal or epithermal neutrons. In large particle accelerators, charged particles are directed against a target, and fission (or fusion) within the target yields a flux of neutrons. Such large facilities are typified by, for example, the Swiss Spallation Neutron Source (SINQ) of the Paul Scherrer Institute (Villigen PSI, Switzerland), the epithermal neutron generating facility at the Massachusetts Institute of Technology, Laboratory for Accelerator Beam Applications (Cambridge, Mass.), as well as the Nuclear Reactor Laboratory at the University of Wisconsin-Madison (Madison, Wis.).

Neutrons can also be produced using isotopic, neutron-emitting sources or small-scale deuterium-tritium neutron generators. Isotopic neutron sources produce a continuous flux of neutrons. The most common isotopic source of neutrons is from spontaneous fission of californium-252 ($^{252}Cf$). The average energy of neutrons emitted from $^{252}Cf$ is 2.3 MeV, so the neutrons must be passed through a moderator to decrease their energy prior to use.

Neutrons can also be produced by mixing an isotope which emits α particle with beryllium-9 ($^9Be$). Neutrons are produced by the (α,n) reaction with beryllium. Common reactions of this type include $^{239}Pu/^9Be$, $^{226}Ra/^9Be$, and $^{241}Am/^9Be$.

As a general proposition, isotopic neutron sources are not preferred for use in the present invention (although they will function perfectly well). While isotopic neutron sources are relatively cheap, they have several insurmountable disadvantages: 1) The neutron output cannot be turned off, thus requiring that the source be contained within bulky shielding at all times. 2) Isotopic neutron sources cannot be pulsed. 3) The energy spectrum of the emitted neutrons is broad and thus not particularly useful in an application where only thermal and epithermal neutrons are required.

Small neutron generators using the deuterium ($^2H$)/tritium ($^3H$) reaction are the most common accelerator-based (as opposed to isotopic) neutron sources. Neutrons are produced by creating deuterium ions and accelerating these ions into a tritium target. (A deuterium target may also be used.) These types of neutron generators are available commercially from many sources, such as Thermo MF Physics (Colorado Springs, Colo.).

Most small deuterium/tritium accelerators are sealed-tube neutron generators. The ion source, the ion optics, and the accelerator target are all enclosed within a vacuum-tight enclosure. The accelerator and ion source high voltages are provided by external power supplies. A control console allows the operator to adjust the operating parameters of the neutron tube. The basic features of a sealed-tube neutron generator are as follows: Ions are generated using a Penning ion source. The Penning source is a low gas-pressure, cold cathode ion source that utilizes crossed electric and magnetic fields. The ion source anode is at a positive potential, either dc or pulsed, with respect to the source cathode. A magnetic field, oriented parallel to the source axis, is produced by a permanent magnet.

The gas pressure in the ion source is regulated by heating or cooling the low-pressure gas. A plasma is formed along the axis of the anode which traps electrons. These electrons, in turn, ionize the gas. The ions are extracted through an exit cathode.

Ions emerging from the exit cathode are accelerated through the potential difference between the exit cathode and the accelerator electrode. The ions pass through the accelerating electrode and strike the target. The target is a thin film of a metal that can form a stable metal hydride containing deuterium and/or tritium (titanium, scandium, and zirconium are most often used). The energy of the ions striking the target results in the production of neutrons.

Gadolinium-Containing Compounds:

Perhaps the most important aspect of the invention is the provision of a gadolinium-containing compound that will serve as the vehicle to convert a thermal neutron flux into nuclear reaction that occurs very close to the DNA of a neoplastic cell. This neutron reaction results in the emission of Auger electrons and γ radiation that causes genetic damage to the neoplastic cell. This damage either kills the cells outright, or inhibits the growth and proliferation of the neoplastic cell.

Of principal importance to the present invention is that the Gd-containing compound must be non-toxic to a mammalian subject and well-tolerated at relatively high concentrations and over a relatively long periods of time (tens of minutes to tens of hours). This is important to enable the tumor cells within a subject to concentrate the Gd-containing compound in sufficient amounts to maximize the effectiveness of the neutron exposure in delivering a fatal dose of radiation to the neoplastic cells. The Gd-containing compound should also be preferentially internalized by neoplastic cells (and most preferably mono-specifically internalized by tumor cells). While this is not a requirement of the invention, specificity in killing or inhibiting the growth of neoplastic cells, while leaving normal cells unaffected is greatly preferred.

The Gd-containing compound may include the naturally-occurring isotopic mixture of gadolinium isotopes, or the compound may be enriched in one or both of the two gadolinium isotopes having a very high neutron cross capture, namely $^{155}Gd$ and $^{157}Gd$.

The preferred compound for use in the present invention is gadolinium diethylene triamine pentaacetic acid (Gd-DTPA) and derivatives thereof. The structure of Gd-DTPA is as follows:

Gd-DTPA

The compound itself is known and approved for use in the United States as an MRI contrast agent in 1988. The complex is anionic and very water soluble (to approximately 0.5 to 1.0 M). Typical counterions to the anion include sodium and N-methylglucaminium. Gd-DTPA is marketed under the trademark "MAGNEVIST" in the United States. It can be purchased in 0.5M and 1.0 M concentrations in an aqueous carrier. At these concentrations, the solutions are hyperosmolar, but as the compound is diluted subsequent to injection, the effect becomes negligible. The LD50 of Gd-DTPA is 20 mmol/kg in rats. Assuming a similar $LD_{50}$ in man, more than 850 g of the complex would have to be injected in order to have a 50% chance of killing a 70 kg human. Thus, the compound is very well tolerated in humans.

Gd-DTPA is very easily manufactured. Mixing $GdCl_3$ with the free DTPA ligand will yield the complex, which can then be separated by HPLC.

Gd-DTPA can also be derivatized very easily and these derivatives can also be used in the present invention. Thus, for example, the bismethylamide of Gd-DTPA, known as Gd-DTPA-BMA or gadodiamide, can also be used in the present invention. It too is available commercially and approved for use as an MRI contrast agent. It is sold under the trademark "OMNISCAN." Its properties are very similar to the parent Gd-DTPA, although it is less soluble and less likely to release free Gd ions than is Gd-DTPA.

Benzyloxyalkyl-substituted Gd-DTPA complexes may also be used. Examples include Gd-BOPTA, a benzyloxylmethyl-substituted Gd-DTPA, and Gd-EOB-DTPA, a benzyloxylethyl-substituted Gd-DTPA. Gd-BOPTA is marketed in Europe as an MRI contrast agent under the trademark "MultiHance."

Phosphate esters of Gd-DTPA, such as gadophostriamine trisodium (also known as MS-325), may also be used. The phosphate moiety bears a large hydrophobic substituent, which makes this compound much more lipophilic than the parent compound. This compound is sold under the trademark "ANGIOMARK."[27]

Biologically-activated derivatives of Gd-DTPA can also be used. For example, phosphorylated sodium aquo(2-(4-(4-hydroxyphenyl)phenoxy)methyl-diethylenetriaminatopentaacetato) gadolineate (III) is a phosphorylated biphenyl derivative of Gd-DTPA. It is administered in the form of an orthophophate that is highly water soluble. Once in the blood, the compound is hydrolyzed by alkaline phosphatase to yield the phenol derivative.

Polymeric DTPA-based agents, such as Gd-DTPA-hydroxypropylpoly(D-lysine) (Gd-DTPA-pdl) may also be used in the present invention. These compounds are biologically interesting because they are membrane impermeable. These compounds can be injected directly into a tumor to be treated and, because they are membrane impermeable, will appear only in the injected tumor cells and their progeny. In terms of specificity, intratumoral injection, with no likelihood of transfer to non-tumor cells, is advantageous.

Gadolinium complexes with the chelating agent 1,4,7,10-tetraazacyclododecane-1,4,7-tricarboxylic acid (DO3A) can also be used in the present invention. The chelate is less than ideal because it is only heptadentate, but it serves as a starting point for many suitable derivatives that can be used in the present invention. Gadolinium complexes with 1,4,9,11-tetraazacyclotetradecane-1,4,9,11-tetraacetic acid (TETA), 1,4,7,10,13-pentaazacyclopentadecane-1,4,7,10,13-pentaacetic acid (PEPA), and 1,4,7,10,13,16-hexaazacyclooctadecane-1,4,7,10,13,16-hexaacetic acid (HEHA) may also be used.

The Gd-containing compound may also be a texaphyrin of the formula:

wherein $R_1$, $R_2$, $R_3$, $R_4$, $R_6$, $R_7$, $R_8$, and $R_9$ are independently selected from the group consisting of hydrogen, halide (other than iodide), hydroxyl, alkyl, aryl, haloalkyl (other than iodoalkyl), nitro, formyl, acyl, hydroxyalkyl, oxyalkyl, oxyhydroxyalkyl, saccharide, aminoalkyl, oxyaminoalkyl, carboxy, carboxyalkyl, carboxyamidealkyl, a site-directing molecule, a catalytic group, or a linkage to a site-directing molecule or to a catalytic group. $R_5$ and $R_{10}$ are independently selected from the group consisting of hydrogen, alkyl, aryl, hydroxyalkyl, oxyalkyl, oxyhyrdroxyalkyl, aminoalkyl, oxyaminoalkyl, carboxyalkyl, carboxyamidealkyl, or a linkage to a site-directing molecule or to a catalytic group. The alkyl, aryl, hydroxyalkyl, oxyalkyl, oxyhydroxyalkyl, saccharide, carboxyalkyl, carboxyamidealkyl, or site-directing subsituent is covalently bonded to the texaphyrin core via a carbon—carbon or a carbon-oxygen bond. The aryl substituent may be a phenyl substituent or a phenyl having a nitro, carboxy, sulfonic acid, hydroxy, oxyalkyl or halide (other than iodide substituent). The substituent on the phenyl group may be added in a synthetic step after the condensation step which forms the macro cycle core. See U.S. Pat. Nos. 5,888,997 and 5,622,946.

As noted in these two patents, exemplary site-directing molecules contemplated in the present invention include, but are not limited to, oligodeoxyribonucleotides, oligoribonucleotide analogs; polyamides including peptides having affinity for a biological receptor, and proteins such as antibodies, low density lipoproteins, the APO protein of lipoprotein; steroids and steroid derivatives; hormones such as estradiol, or histamine; hormone mimics such as morphine; and macrocycles such as sapphyrins and rubyrins. An oligonucleotide may be derivatized at the base, the sugar, the ends of the chain, or at the phosphate groups of the backbone to promote in vivo stability. Modification of the phosphate groups is preferred because phosphate linkages are sensitive to nuclease activity. Preferred derivatives are methylphosphonates, phosphotriesters, phosphorothioates, phosphoramidates and the like. Additionally, phosphate linkages may be completely substituted with non-phosphate linkages such as amide linkages. Appendages to the ends of the oligonucleotide chain also provide exonuclease resistance. Sugar modifications may include alkyl groups attached to an oxygen of a ribose moiety in a ribonucleotide. In particular, the alkyl group is preferably a methyl group and the methyl group is attached to the 2' oxygen of the ribose. Other alkyl groups may be ethyl or propyl. It is understood that the terms "nucleotide" and "oligonucleotide", as used herein, refer to both naturally-occurring and synthetic nucleotides, poly- and oligonucleotides and to analogs and derivatives thereof.

The term "texaphyrin-oligonucleotide conjugate" means that an oligonucleotide is attached to the texaphyrin in a 5' or 3' linkage or both types of linkages to allow the texaphyrin to be an internal residue in the conjugate. The oligonucleotide or other site-directing molecule may be attached either directly to the texaphyrin via a linker, or a couple of variable length. During treatment, for example, the texaphyrin portion of a texaphyrin metal complex-oligonucleotide conjugate is envisioned as being placed in the vicinity of the targeted tissue upon binding of the oligonucleotide to its complementary DNA.

A "linkage" is the covalent product formed by reaction of a reactive group designed to attach covalently to another molecule at a distance from the texaphyrin macro cycle. Exemplary linkages are amides, amine, thioether, ether, or phosphate covalent bonds. For example, oligonucleotides and other site-directing molecules are covalently bonded to the texaphyrin via a carbon-nitrogen, carbon-sulfur, or a carbon-oxygen linkage.

The term "a peptide having affinity for a biological receptor" means that upon contacting the peptide with the biological receptor, for example, under appropriate conditions of ionic strength, temperature, pH and the like, specific binding will occur. The interaction may occur due to specific electrostatic, hydrophobic, entropic or other interaction of certain amino acid or glycolytic residues of the peptide with specific amino acid or glycolytic residues of the receptor to form a stable complex under the conditions effective to promote the interaction. The interaction may alter the three dimensional conformation and the function or activity of either or both the peptide and the receptor involved in the interaction. A peptide having affinity for a biological receptor may include an endorphin, an enkephalin, a growth factor, e.g., epidermal growth factor, poly-L-lysine, a hormone, a peptide region of a protein and the like. A hormone may be estradiol, for example.

The term "catalytic group", as used herein, means a chemical functional group that assists catalysis by acting as a general acid, a Bronsted-Lowry acid, a general base, Bronsted-Lowry base, a nucleophile, or any other means by which the activation barrier to reaction is lowered or the ground state energy of the substrate is increased. Exemplary catalytic groups contemplated in the present invention include, but are not limited to, imidazole, guanidine, substituted saccharides such as D-glucosamine, D-mannosamine, D-galactosamine, D-glucamine and the like; amino acids such as L-histidine and L-arginine; derivatives of amino acids such as histamine; polymers of amino acids such as poly-L-lysine, (LysAla)n, (LysLeuAla)n where n is from 1–30 or preferably 1–10 or most preferably 2–7, and the like, derivatives thereof, and texaphyrin metal complexes.

The Gd-containing compound may be administered alone or in combination with pharmaceutically acceptable carriers, in either single or multiple doses. Thus, the Gd-containing compound is delivered to a mammalian subject in the form of a pharmaceutical composition comprising an active Gd-containing compound (or a pharmaceutically-acceptable salt thereof) in combination with an acceptable carrier therefor and optionally with other therapeutically-active ingredients or inactive accessory ingredients. The carrier must be pharmaceutically-acceptable in the sense of being compatible with the other ingredients of the formulation and not deleterious to the recipient. The pharmaceutical compositions include those suitable for oral, topical, inhalation, rectal, and parenteral (including subcutaneous, intramuscular, intravenous, intracranial, and intratumoral) administration. As used herein, "pharmaceutically acceptable carrier" includes any and all solvents, dispersion media, coatings, antibacterial and antifungal agents, osmolality/osmolarity modifiers, absorption-delaying agents, and the like. The use of such media and agents for pharmaceutically-active substances is well known in the art. Supplementary active ingredients can also be incorporated into the compositions.

The formulations may conveniently be presented in unit dosage form and may be prepared by any of the methods well known in the art of pharmacy. The term "unit dosage" or "unit dose" is denoted to mean a predetermined amount of the Gd-containing compound sufficient to be effective for treating an indicated condition or to arrive at a given final intracellular concentration of the compound, or to deliver a desired radiation dose subsequent to neutron capture. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

Formulations of the present invention suitable for oral administration may be presented as discrete units such as capsules, cachets, tablets, boluses or lozenges, each containing a predetermined amount of the Gd-containing compound; as a powder or granules; or in liquid form, e.g., as an aqueous solution, suspension, syrup, elixir, emulsion, dispersion, or the like.

A tablet may be made by compression or molding, optionally with one or more accessory ingredients. Compressed tablets may be prepared by compressing in a suitable machine the Gd-containing compound in a free-flowing form, e.g., a powder or granules, optionally mixed with accessory ingredients, e.g., binders, lubricants, inert diluents, surface active or dispersing agents. Molded tablets may be made by molding in a suitable machine a mixture of the powdered Gd-containing compound with any suitable carrier.

Formulations suitable for parenteral administration conveniently comprise a sterile preparation of the Gd-containing compound in, for example, water for injection, saline, a polyethylene glycol solution, suitable vegetable oils, and the like, which is preferably isotonic with the blood of the recipient. As noted above, the DTPA complexes are anionic and thus tend toward hyperosmolarity. Thus, it is not required that the formulations for injection be isotonic as administered, but preferably should approach isotonicity upon dilution, consistent with delivering a suitably large dose of the Gd-containing compounds. Aqueous solutions for injection should be suitably buffered if necessary and the liquid diluent itself first rendered isotonic with sufficient saline or glucose.

The pharmaceutical forms suitable for parenteral injection include sterile aqueous solutions or dispersions and sterile powders that can be dissolved or dispersed extemporaneously into a sterile injectable solution or dispersion. In all cases, the dosage form must be sterile and must be fluid to the extent that it can be injected using standard equipment. It must be stable under the conditions of manufacture and storage and must be preserved against the contaminating action of microorganisms, such as bacteria and fungi. Proper fluidity can be maintained, for example, by using a coating (such as lecithin), by maintaining the required particle size in the case of dispersions, and by using surfactants.

Preventing microbial growth can be accomplished using various well-known antibacterial and antifungal agents, such as parabens, chlorobutanol, phenol, sorbic acid, thimerosal, and the like. In many cases, it will be preferable to include isotonic agents, for example, sugars such as mannitol or dextrose or sodium chloride. A more preferable isotonic agent is a mannitol solution of about 2–8% concentration, and, most preferably, of about 5% concentration. Prolonged absorption of the injectable compositions can be can be accomplished using agents such as aluminum monostearate and gelatin.

Sterile injectable solutions are prepared by incorporating one or more Gd-containing compounds in the required amount in the appropriate solvent with various of the other ingredients enumerated above, followed by sterilization. Generally, dispersions are prepared by incorporating the various sterilized ingredients into a sterile vehicle which contains the basic dispersion medium and any other ingredients. In the case of sterile powders used to prepare sterile injectable solutions, the powders can be prepared via vacuum-drying and freeze-drying techniques that yield a powder of the Gd-containing compound plus any additional desired ingredients. These types of formulations (a concentrated solution or solid containing one or more Gd-containing compounds, which upon dilution with an appropriate solvent gives a solution or dispersion suitable for parenteral administration) are very convenient, easy to transport and store, have a long shelf-life, and can be prepared immediately prior to use.

Preparations for topical or local applications comprise aerosol sprays, lotions, gels, ointments, suppositories etc., and pharmaceutically-acceptable vehicles therefore such as water, saline, lower aliphatic alcohols, polyglycerols such as glycerol, polyethylene glycerol, esters of fatty acids, oils and fats, silicones, and other conventional topical carriers. In topical formulations, the subject compounds are preferably utilized at a concentration of from about 0.1% to 5.0% by weight.

Compositions suitable for rectal administration, comprise a suppository, preferably bullet-shaped, containing the Gd-containing compound and pharmaceutically-acceptable vehicles therefore such as hard fat, hydrogenated cocoglyceride, polyethylene glycol and the like. In suppository formulations, the subject compounds are preferably utilized at concentrations of from about 0.1% to 10% by weight.

Compositions suitable for rectal administration may also comprise a rectal enema unit containing the active ingredient and pharmaceutically-acceptable vehicles therefore such as 50% aqueous ethanol or an aqueous salt solution which is physiologically compatible with the rectum or colon. The rectal enema unit consists of an applicator tip protected by an inert cover, preferably comprised of polyethylene, lubricated with a lubricant such as white petrolatum and preferably protected by a one-way valve to prevent back-flow of the dispensed formula, and of sufficient length, preferably two inches, to be inserted into the colon via the anus. In rectal formulations, the Gd-containing compounds are preferably utilized at concentrations of from about 5.0–10% by weight.

Useful formulations also comprise concentrated solutions or solids containing the Gd-containing compound which upon dilution with an appropriate solvent, preferably saline, give a solution suitable for rectal administration. The rectal compositions include aqueous and non-aqueous formulations which may contain conventional adjuvants such as buffers, bacteriostats, sugars, thickening agents and the like. The compositions may be presented in rectal single dose or multi-dose containers, for example, rectal enema units.

Compositions suitable for administration by inhalation include formulations wherein the Gd-containing compound is a solid or liquid admixed in a micronized powder having a particle size in the range of about 5 microns or less to about 500 microns or liquid formulations in a suitable diluent. These formulations are designed for rapid inhalation through the oral passage from a conventional delivery systems such as inhalers, metered-dose inhalers, nebulizers, and the like. Suitable liquid nasal compositions include conventional nasal sprays, nasal drops and the like, of aqueous solutions of the active ingredient(s).

In addition to the aforementioned ingredients, the pharmaceutical formulations may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

The amount of Gd-containing compound required to be effective for any indicated condition will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular Gd-containing compound to be administered. In general, a suitable effective dose is in the range of about 0.1 to about 500 mg/kg body weight per treatment (i.e. per exposure to neutrons), preferably in the range of about 5 to about 350 mg/kg per day, calculated as the non-salt form of the Gd-containing compound. The total dose may be given as a single dose, multiple doses, or by intravenous infusion for a selected duration. Dosages above or below the range cited above are within the scope of the present invention and may be administered to the individual patient if desired and necessary.

Treating Mammalian Subjects:

In practice, the present invention proceeds as follows:

Using Gd-DTPA as an exemplary Gd-containing compound, and a mammal suffering from glioblastoma multiforme as an exemplary subject, the subject is first placed in proximity with a neutron source and is then injected (intravenously, intracranially, or intratumorally) with an amount of the Gd-DTPA sufficient to raise the level of Gd within the glioblastoma cells. It is preferred that the amount of the Gd-containing compound be sufficiently large to result in an intracellular concentration of 250 $\mu$g/ml of Gd. At this concentration, the neutron capture reaction yields a suitably powerful dose of Auger electrons and gamma radiation to inhibit further growth of the glioblastoma cells.

Once injected, Gd-DTPA (as well as many of its derivatives) behaves similarly to other biologically-inert compounds. Gd-DTPA has no appreciable protein-binding, nor does it exhibit any inhibitory interaction with enzymes. Likely due to its anionic nature, in higher concentrations and on prolonged exposure, Gd-DTPA leads to a weak, reversible intravascular hemolysis. Following intravenous administration, Gd-DTPA is distributed rapidly in the extracellular space, where it is internalized by glioblastoma cells. Unabsorbed Gd-DTPA is eliminated unchanged by glomerular filtration via the kidneys. It has been observed in humans that the pharmacokinetics of Gd-DTPA are independent of the dose. At 6 hours post-injection in man, an average of about 83% of the Gd-DTPA dose is eliminated renally. At 5 days post-injection in man, approximately 91% of the dose is found in the urine.

The dosage may be administered as a single dose, or in multiple doses, or in a continuous fashion, such as by intravenous drip (continuous administration being preferred to maintain a uniformly high concentration of Gd in the glioblastoma cells). Once the subject has been dosed with the Gd-containing compound, the subject is then shielded appropriately, and the subject's head (or the otherwise affected region) is exposed to a flux of thermal neutrons.

Exposure to the neutron flux must be consistent with federal regulations and sound nuclear medicine practices. Neutrons are ionizing radiation and thus must be handled with all due precautions. Generally, the subject should be exposed to a thermal neutron flux of from about 1 to about $10 \times 10^8$ n/cm$^2$s, with about $3 \times 10^8$ n/cm$^2$s being preferred. At $3 \times 10^8$ n/cm$^2$s, the γ average dose is about 3.2 Gy/h. This range of neutron flux is preferred, but neutron doses above and below this range are within the scope of the invention.

Subsequent to neutron beam exposure, he subject is then observed for a number of days. The subject can then be examined to determine the extent of glioblastoma cell damage caused as a result of the GdNCT treatment.

EXAMPLES

The following Examples are included solely to provide a more complete understanding of the invention disclosed and claimed herein. The Examples do not limit the scope of the invention in any fashion.

Materials and Methods:

Cell Culture and Gd-DTPA Uptake:

Primary cells were derived from tissue extracted from a patient undergoing surgery for resection of a right temporal lobe tumor. The tumor was classified as glioblastoma multiforme according to the WHO criteria.[17] The tissue was finely triturated and treated with a physiological trypsin solution (0.25% Trypsin, 1 mM EDTA) for 20 mm. at 36° C. to obtain a suspension of dissociated cells. The harvested cells were propagated in Dulbecco's modified Eagle's Medium (DMEM) supplemented with 10% FBS, at 36.5° C., 5% $CO_2$, and humidified atmosphere. Cells were always re-plated in the same media once they reached confluence.

The established cell line (designated "TB 10") was immunohistochemically characterized and the cells stained positively for Glial Fibrillary Acidic Protein. Staining of the cells for neuronal (Neuron Specific Aneles, NSE; Synaptophisin; S 100), endothelial (factor VIII related antigen, F-VIII RAG; CD31), epithelial (epithelial membrane antigen, EA.), lymphoid/hematopoietic (CD34, CD45, MAC387) and cytoskeletal proteins (Vimentin, Cytokeratin) was negative. It was therefore concluded that the cells are homogeneously glial cells. At the time of exposure to Gd, the cells were in the exponential growth phase.

Starting 24 hours after plating, Gd-DTPA (Schering) was added to the culture media to obtain concentrations of 1 to 25 mg/ml in the culture medium, at subsequent points in time. Exposure times varied from 0 to 120 hours. The different cell cultures for spectromicroscopy, ICP-MS, neutron bombardment and TOF-SIMS experiments were prepared as follows.

1) For spectromicroscopy experiments, two series of cell cultures from different passages were prepared, in which $5 \times 10^4$ cells/cm$^2$ were plated in 35 mm plastic Petri dishes, each containing 4 to 5 gold-plated stainless steel substrates (5 mm diameter). The Gd exposure concentration was 10 mg/ml and the exposure times were 0 to 72 hours. At the end of the exposure periods, all dishes were carefully washed three times with phosphate buffered saline (PBS) to remove all unbound Gd-DTPA, fixed in 4% paraformaldheyde in PBS for 20 minutes, and then washed in Milii Q water. The samples were then air-dried at room temperature and etched by exposure to UV light from a low-pressure mercury lamp in the presence of ozone. $UV/O_3$ etching selectively removes carbon and nitrogen from the cells without architectural distortion, thereby preserving the micro localization of all other elements.[18,19] In the present study, etching was employed to reveal the local (i.e., nuclear) concentration of Gd which would otherwise not be detectable with x-ray absorption spectroscopy. The cell cultures were etched for 116 hours, at a distance of 5 mm from the UV lamp.

2) For ICP-MS experiments to test Gd uptake vs. exposure time, five series of cell cultures from different passages were plated in 35 mm plastic Petri dishes at a density of $5 \times 10^4$ or $1 \times 10^5$ cells/cm$^2$, and exposed to 10 mg/ml Gd-DTPA, for 0 to 120 hours. The different cell densities were chosen to investigate the effect of confluence on Gd uptake. At the end of the Gd-incubation period, the cells were carefully washed three times with PBS before adding 1 ml of 1 N $HNO_3$ to the dishes. After 60 minutes digestion at room temperature in a rocking platform, cells and liquid were collected in clean plastic tubes.

3) For ICP-MS experiments to test Gd uptake vs. exposure concentration, three series of cell cultures (each one in duplicate) from different passages were plated in 35 mm plastic Petri dishes at a density of $5 \times 10^4$ cells/cm$^2$ and exposed to 1 mg/ml, 5 mg/ml, 10 mg/ml, or 25 mg/ml Gd-DTPA, for 72 hours, beginning 24 hours after plating. At the end of the exposure period, the cells were washed three times in PBS, then digested in 1 ml of 1 N $HNO_3$. The standard deviation of the ICP-MS experiments was calculated on the 6 culture series.

4) For ICP-MS experiments to test Gd release after Gd exposure, two series of cell cultures from different passages were plated in 35 mm plastic Petri dishes at a density of $5 \times 10^4$ cells/cm$^2$ and exposed to 10 mg/ml Gd-DTPA, for 72 hours, beginning 24 hours after plating. At the end of the exposure period, the media were all replaced with 2 ml of modified Puck's saline (137 mM NaCl, 5.3 mM HCl, 6.1 mM D+Glucose, 0.1 mM $CaCl_2$, 0.6 mM $MgCl_2$, 10 mM HEPES; pH 7.4) and kept at room temperature for 0–8 hours, prior to harvesting in 2 ml 1 N $NO_3$ for ICP-MS analysis. The standard deviation of the ICP-MS experiments on the 2 culture series was within 10%.

5) For neutron bombardment, two series of cell cultures (each one in duplicate) from different passages were plated in plastic "NUNC"-brand flasks (Nalge Nunc International, Rochester, N.Y.) (NUNCLON, 25 cm$^2$culture area) at a density of $1 \times 10^4$ cells/cm$^2$ and exposed to no Gd-DTPA, 1 mg/ml, 5 mg/ml, or 10 mg/ml GdDTPA, for 72 hours, beginning 24 hours after plating. At the end of the exposure period, the growth media were removed and the flasks filled with Puck's modified saline, in which the cells remained for two hours before neutron bombardment. The cells were then irradiated for one hour under a thermal neutron flux of $3 \times 10^8$ n/cm$^2$s (nominal power 5 kW), at the ENEA's (Ente per le Nuove Tecnologie, L'Energia e L'Ambiente, Rome, Italy) TAPIRO fast Reactor. The fast neutron flux at the center of the irradiation chamber (20 cm$^3$ cube) was negligible, while the γ average dose was 3.2 Gy/h.[20] Two hours later, the cells were detached from the plates, and cell survival was measured by cell counting and by the colorimetric MTT assay. The standard deviation of cell counting results on the four culture series was within 10%.

The structure of Gd-DTPA is as follows:

Gd-DTPA

At the end of the culturing and the exposure periods, all dishes were carefully washed three times with phosphate buffered saline (PBS) to remove all the Gd-DTPA not taken up by the cells, fixed in 4% paraformaldheyde in PBS for 20 minutes, then washed in distilled, deionized water. The samples were then air dried at room temperature and etched in a UV/ozone environment as described below. Two samples coming from different re-plating steps were prepared for each exposure time. For ICP-MS experiments, five series of samples were plated in 35 mm plastic Petri dishes at a density of $5\times10^4$ or $1\times10^5$ cells/cm$^2$. The different cell densities were chosen to investigate the effect of confluence on Gd uptake. At the end of the Gd-incubation period, the cells were carefully washed three times with PBS before adding 1 ml of 1N $HNO_3$ to the dishes. After 60 minutes digestion at room temperature in a rocking platform, cells and liquid were collected in clean plastic tubes.

ICP-MS:

Inductively Coupled Plasma Mass Spectrometry (ICP-MS) provides a quantitative analysis of the concentration of an element in aqueous solution and has a sensitivity of 0.02 ppb or better for Gd[21]. The analyte concentration is proportional to the number of ions of a specific element that reach the mass spectrometer, from the vaporized solution at 800° C. The analysis of cell samples in solution was performed after digestion in nitric acid and sonication. A single ICP-MS measurement represents the average of 7 replicates from the same liquid sample, with a very small error (less than 5%). The gadolinium concentrations presented in FIG. 1 at each time point were averaged across five series of cultures, ensuring that the values are correctly scaled to account for cell population differences and dilutions (based on the measurement that a volume of 1 μl contains 70,000–80,000 cells). The errors on these mean values are the standard deviations between the five cultures at each exposure time, and represent the biological variability.

MEPHISTO Spectromicroscopy:

Microchemical analysis of the etched cell cultures was performed with the custom-built MEPHISTO (Microscope á Emission de PHotoélectrons par Illumination Synchrotronique de Type Onduleur) X-ray photoelectron emission microscope (X-PEEM), which uses an electron optics system (SpectroMicroTech, Orlando, Fla., USA) to form a magnified image of the photoelectrons emitted by a specimen under soft x-ray illumination. The image magnification is continuously variable up to 8000x, and the optimum lateral resolution is 20 nm[15]. The image pixel intensity (corresponding to total photoelectron yield, per unit area, per unit time) is recorded as a function of photon energy. Such spectra, in fact, reflect the x-ray absorption coefficient of the specimen surface and are hence referred to as x-ray absorption spectra. The position and line-shape of spectral features provide element identification and chemical state information. Spectra can be acquired simultaneously from regions selected on the real time image of the sample surface, and the probed depth is on the order of 100 Å. For this work, the MEPHISTO X-PEEM was mounted on the HERMON beamline of the University of Wisconsin-Madison Synchrotron Radiation Center (Stoughton, Wis.).

MEPHISTO micrographs acquired at a specific photon energy were processed in Adobe Photoshop 5.0 software for Macintosh to enhance the contrast and add a scale bar. Images showing the spatial distribution of Gd and Ca were obtained by digital ratio of the pixel intensity of on-absorption peak to pre-peak micrographs.

MEPHISTO spectra were saved as text files and plotted in Kaleidagraph 3.0.4 software for Macintosh. Spectra taken from cell structures and substrate areas were normalized by dividing by a third-order polynomial fit to the raw data. Because of the weak gadolinium signal and high background in the x-ray absorption spectra, the systematic errors introduced by this simple normalization procedure are small compared to other experimental errors. Although in general the x-ray absorption spectra acquired in MEPHISTO may contain complicated dependencies on sample, monochromator, and beamline characteristics, the Gd 3d peaks are far from the absorption peaks of other elements, and the output of the HERMON monochromator is extremely smooth at these photon energies. Hence spectra normalized as described produce a plot dependent only on the Gd line-shape and local concentration.

A comparison of ICP-MS and MEPHISTO data, determines the calibration of the MEPHISTO analysis, and therefore quantitative information on the Gd concentration at the microscopic level. To obtain the local Gd concentration in ppm (1 ppm=1 μg/ml), the Gd $3d_{5/2}$ normalized peak height is multiplied by $10^6$ for unashed samples or by $10^5$ for ashed samples, since ashing enhances the relative Gd concentration by a factor of 10. These factors were derived from the matching of MEPHISTO data from whole cells to the ICP-MS cell-bulk data, so that they quantitatively overlap.

This allows comparisons to be made of local Gd concentrations between, for example, different cells and between different sub-cellular structures. It also enables the ICP-MS average results on individual cells to be verified (as reported in FIG. 1).

A total of approximately 300 spectra from whole cells were obtained, including regions of cytoplasm, nucleus, or substrate. The acquisition time for each set of spectra being roughly 3 to 6 hours. For the purpose of comparing the two sets of Gd uptake vs. exposure time measurements, (those acquired in MEPHISTO vs. acquired via ICP-MS), the spectral data from all cell regions but not the substrate region was considered. Note that there was no gadolinium signal detectable from any substrate region. Of the MEPHISTO acquisition areas, 47 were categorized as coinciding with nuclei and 80 with cytoplasm. No gadolinium signal was detected from the 0 hours sample, either with MEPHISTO or ICP-MS analysis, and no distinction was made between nuclear and cytoplasmic regions in this sample.

TOF-SIMS:

Time of Flight Secondary Ion Mass-Spectrometry (TOF-SIMS), another technique for microchemical analysis[22] was utilized to validate data from MEPHISTO spectromicroscopy, in addition to the ICP-MS data. Cell samples were bombarded with either 15 or 25 keV $Ga^+$ ions, focused in a microscopic beam, which induced desorption of the surface atoms. The emitted ions were then accelerated, and detected by a high resolution mass spectrometer. By scanning the microscopic Ga ion beam, TOF-SIMS produced images of the cell surface, and distribution maps of specific element isotopes, with a spatial resolution of 1 ppm. High resolution mass spectra were obtained from microscopic areas, selected as the region of interest in the cell images, to allow quantitative comparison of Gd concentration in sub-cellular regions.

Results

Figure 1:
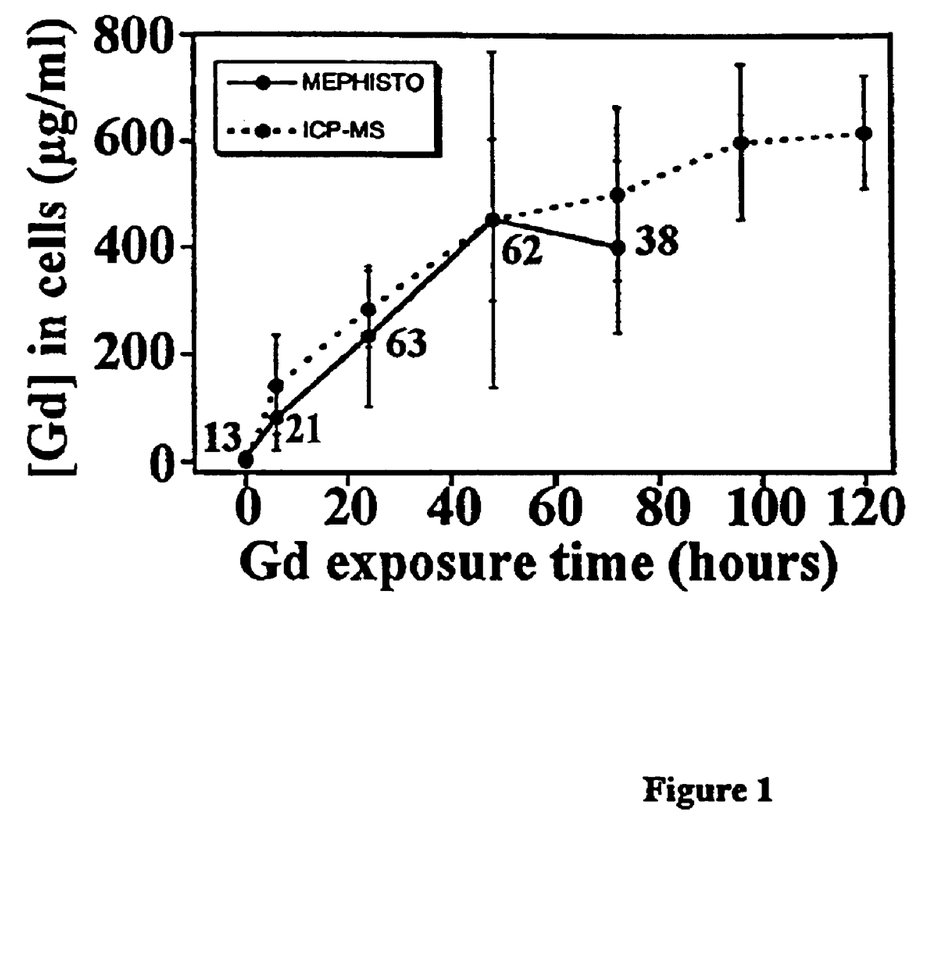
FIG. 1 is a gadolinium uptake curve as a function of exposure time, measured by ICP-MS analysis of entire cell cultures (approximately $10^6$ cells) and by MEPHISTO analysis of whole-cell regions. The ICP-MS data average the results from five experimental series, and the error bars represent the standard deviation. The MEPHISTO data average the gadolinium signal intensities acquired on individual cells taken from two experimental series. The number of individual cells contributing to each data point is reported next to the point, and the error bars represent the standard deviation. Larger error bars correspond to MEPHISTO data.

I. Bulk Uptake Kinetics:

Mass Spectrometry vs. Absorption Spectroscopy:

In the dashed curve of FIG. 1, the quantitative ICP-MS data acquired on five series of cell cultures is shown. These cells were exposed to Gd-DTPA for up to 120 hours. The five results at each time point were averaged to produce FIG. 1, which has been re-scaled to show the cellular gadolinium concentrations before digestion in nitric acid for ICP-MS analysis. Not all cell cultures contained the same number of cells (in order to resolve any effects of cell density on the uptake kinetics), but population differences were accounted for when calculating the cellular Gd concentrations. FIG. 1 shows that the cellular Gd concentration increases with the exposure time.

The solid curve of FIG. 1 shows the corresponding gadolinium uptake kinetics in two parallel series of cell cultures, exposed to Gd-DTPA for 0 to 72 hours and analyzed in MEPHISTO by x-ray absorption spectroscopy of individual cells. The results closely match the curve obtained from ICP-MS. The unexposed samples show no gadolinium signal, while at other time points the gadolinium concentration increases with the exposure time.

To make a comparison between the MEPHISTO and ICP-MS uptake curves, the normalized Gd $3d_{5/2}$ peak intensities (arbitrary units) were scaled by a factor of $10^6$ to match the ICP data (in mg/ml in the original cells). This empirical calibration factor contains all the linear experimental response contributions (x-ray beam intensity, electron optical transmission function, etc.) to the final signal. Because the samples studied in MEPHISTO were etched before analysis, and because no independent reference samples of known Gd concentration could be analyzed, it is not possible to convert directly the MEPHISTO absorption intensities into absolute gadolinium concentrations in the living cells. However, the careful normalization procedure enables relative concentration comparisons to be made.

The errors in the MEPHISTO and ICP-MS data do not have identical sources, so a distinction can be made between measurement errors and biological variability. For both techniques, the error on an individual measurement (as measured by replicate measurements) is acceptably small: roughly 5–25% for x-ray absorption measurements and <5% for ICP-MS. Note that a single ICP-MS analysis takes place on $10^6$ cells, while a single MEPHISTO measurement considers only a fraction of a single cell. The errors shown on the ICP-MS data are much larger than the single measurement uncertainty because even cultures exposed with identical protocols do not give the same result. This is due to a combination of errors in the experimental practice, and intrinsic biological variation in the system. The assertion that biological variability is the major contribution to the error bars on the ICP-MS data is in fact confirmed by the MEPHISTO analysis, which directly captures the substantial variance in Gd uptake over many individual cells, leading to equally substantial error bars in this data. Because of all the sources of experimental uncertainty, MEPHISTO analysis was performed systematically on many cells in order for the results presented to have statistical weight.

Gd-DTPA Toxicity and the Effect of Cell Confluence:

Two effects that may affect the Gd-DTPA uptake kinetics were examined: compound toxicity and cell density. Three independent series of cell cultures were grown at different densities and exposed for up to 120 hours. Cell counting performed at the end of the incubation time either in control or in Gd-treated cultures gave the same cell number. This demonstrated that under these experimental conditions the cells were viable and proliferated at the same rate. Gd-DTPA did not affect cell growth, hence it did not show any cytotoxic or cytostatic effect. Therefore it can be inferred that Gd-DTPA does not release the toxic $Gd^{3+}$ ion that is known to reduce cell survival.

In addition, some of the cells exposed to Gd-DTPA for 120 hours were re-plated. It was found that after one-week, they grew normally and did not appear to be morphologically different from the controls.

The ICP-MS results prove that high cell density (confluence at the end of the experiment) has no detectable effect on the quantity of gadolinium internalized by tumor cells. The curves of gadolinium concentrations vs. time at each density (correctly scaled to number of cells) could be overlapped within the error bars of FIG. 1.

Figure 2:
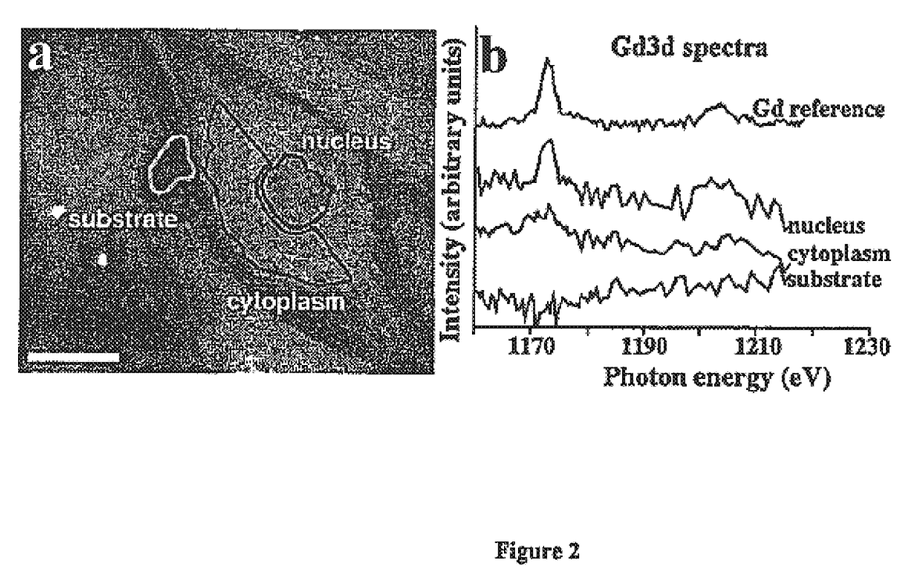
FIG. 2A is a calcium distribution map of a group of cells grown on a gold substrate and exposed to Gd-DTPA for 72 hours. Areas containing calcium appear bright. Note the calcium deficiency in the nucleus, and the absence of calcium between cells (substrate regions). Scale bar=20 $\mu$m.
FIG. 2B is a Gd 3d x-ray absorption spectrum acquired simultaneously from the areas shown in FIG. 2A, plus the spectrum from a Gd-DTPA reference sample (top curve). No gadolinium was detected from the substrate region. The strongest Gd signal was obtained from the cell nucleus. This result was observed for individual cells in MEPHISTO, confirmed with independent TOF-SIMS analysis, and shown to be statistically significant by serial analysis of many cells in MEPHISTO.

Gadolinium Uptake in Nucleus vs. Cytoplasm:

The agreement between ICP-MS and MEPHISTO Gd uptake curves established that x-ray absorption spectroscopy can be used to measure relative gadolinium concentration. The spectra were then sorted into two groups: those from cell nuclei and those from cytoplasm. In the cell cultures studied, the position of the nucleus within a cell was usually evident from the morphology apparent in the photoelectron micrographs. This was confirmed by the acquisition of calcium distribution maps, which showed the nucleus as a calcium-deficient area within the cell. In some photoelectron micrographs the location of the nucleus was not obvious as there was no clear (topographical) nuclear boundary. Where it was not possible to identify the position of the nucleus, the spectra were excluded from analysis. An example of MEPHISTO analysis of an individual cell is presented in FIG. 2.

FIG. 2A shows a region of one of the cell culture samples (72-hour exposure) imaged by MEPHISTO to show the distribution of calcium. The calcium distribution was obtained by a digital ratio of a micrograph at 354 eV (on the Ca $2p_{3/2}$ peak) to one at 352 eV (before peak). The marked cell clearly shows a central calcium deficient nucleus. FIG. 2B shows the corresponding Gd 3d spectra, along with a reference spectrum from Gd-DTPA. No gadolinium was detected from the substrate region of this or any other culture. The spectra of FIG. 2B were acquired simultaneously (except for the Gd reference) and subsequently normalized as described hereinabove.

The spectra have been displaced for clarity and contain some noise, but show that the highest concentration (intensity of the Gd $3d_{5/2}$ absorption peak at 1175 eV) of Gd is present in the cell nucleus.

A compilation of similar analyses on approximately 100 individual cells throughout the series of cultures showed a tendency for higher Gd concentration in nuclei than in cell cytoplasm, as shown in Table 1. This result was investigated with the Student t-test and found to be significant or highly significant at two time points, 24 and 72 hours.

TABLE 1

| | Exposure Time | | | |
|---|---|---|---|---|
| | 6 hrs | 24 hrs | 48 hrs | 72 hrs |
| Ratio: Gd nucleus/Gd cytoplasm | 1.6 | 2.1 | 1.0 | 1.3 |
| # data from nuclei | 3 | 11 | 15 | 18 |
| # data from cytoplasm | 10 | 20 | 25 | 25 |
| Student t-test for Gd nucleus/Gd cytoplasm | not significant | highly significant | not significant | significant |

Table 1. Ratio of the mean concentrations of gadolinium in nuclei vs. cytoplasm, for each time of exposure to Gd-DTPA. The concentration on each individual cell nucleus or cytoplasm was obtained from the $3d_{5/2}$ peak height of normalized MEPHISTO Gd spectra. The results for nuclei and cytoplasms were averaged over the number of analyzed regions reported in table, and the ratio calculated. At each time point the Student t-test was employed to determine if the increase in Gd in nuclei was statistically significant. At two time points, 24 and 72 hours, there were significantly higher Gd concentration in nuclei.

The results obtained in MEPHISTO were corroborated by the TOF-SIMS) data, an independent technique to evaluate elemental distributions at a microscopic scale. Two cells were studied from one of the etched 72-hour exposure samples used in the MEPHISTO experiment. The results obtained on these two cells are reported in Table 2. Note in the table that the concentration of Gd is consistently higher in nuclei than in cytoplasm.

TOF-SIMS analysis of a non-etched cell at the nucleus position (also Gd-exposed for 72 hours), was performed before and after strong sputtering to probe the Gd concentration on the membrane and inside the nucleus. The total Gd ion yield, calculated as for the first column of Table 2, gave 0.055 cts/s on the unsputtered sample.

Figure 3:
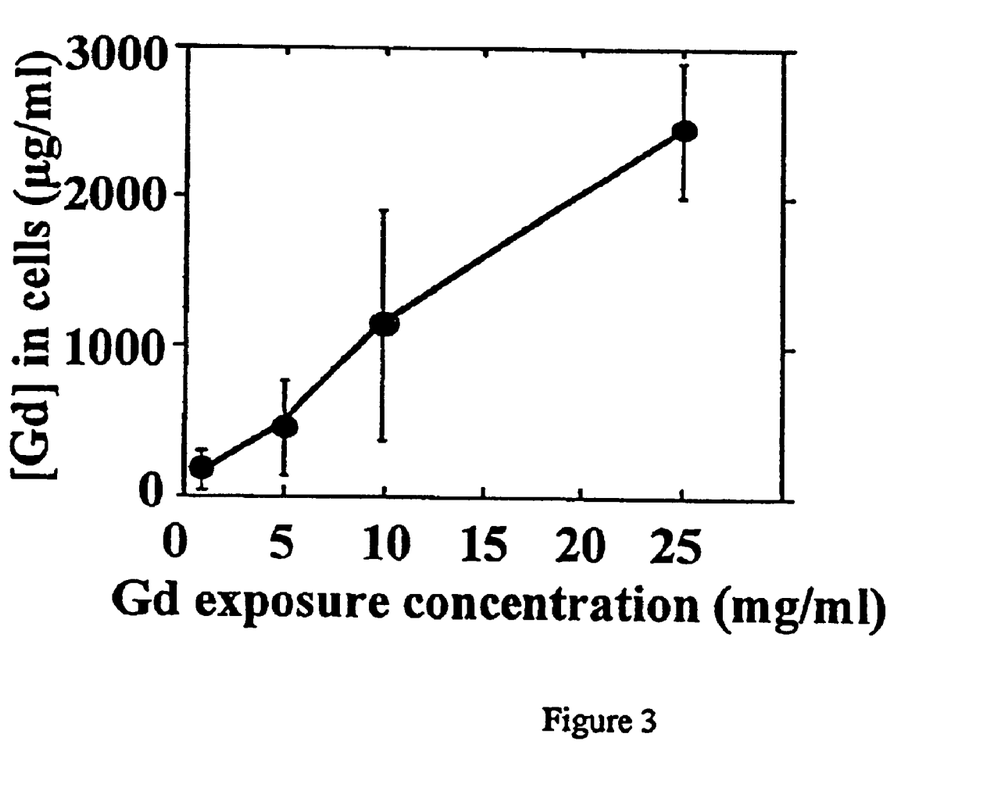
FIG. 3 is a graph depicting gadolinium concentration, measured by ICP-MS, in glioblastoma cells exposed to the indicated Gd-DTPA concentrations for 72 hours. The error bars are the standard deviations calculated over 6 cell cultures. The Gd uptake clearly increases with the Gd-DTPA exposure concentration.

After 30 second sputtering (with 25 keV Ga~ ions) to remove surface contamination, the total Gd ion yield from the cell membrane was 0.182 cts/s. After 16 minute sputtering to penetrate about 1 pm into the nucleus, the total Gd ion yield was 1.844 cts/s. These data confirm that Gd-DTPA had entered the cell and the nucleus, and was not simply membrane-bound.

culture media, the cultures were treated with different concentrations of Gd-DTPA for the same exposure period of 72 hours, and then analyzed with ICP-MS. The results presented in FIG. 3 indicate that the concentration of uptaken Gd increases with the exposure concentration.

Cell counting in the parallel cultures exposed to different concentrations of Gd-DTPA and unexposed controls indicated the same number of cells in each vessel, demonstrating that GdDTPA was not cytotoxic or cytostatic.

Figure 4:
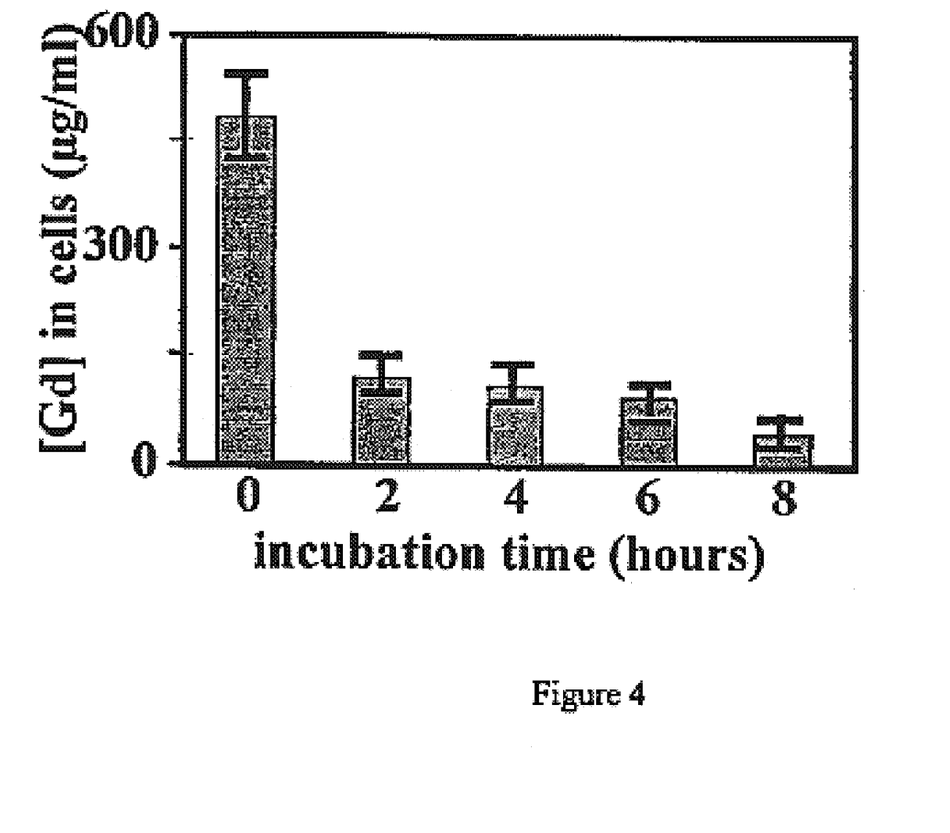
FIG. 4 is a graph depicting gadolinium retention by glioblastoma cells, measured by ICP-MS, and averaged over two series of cell cultures. Standard deviation was less than 10%. The cell cultures were all exposed to the same Gd-DTPA concentration (10 mg/ml) for 72 hours. After the incubation time, the Gd-DTPA-containing media were removed and replaced with a physiological solution. Incubation continued for the reported periods of time at room temperature. Two to four hours after removal of Gd-DTPA, the intracellular retained Gd concentration was stable (140 $\mu$g/ml).

Gd Release:

A significant parameter for an effective Gd-NCT is the retention time of Gd in tumor cells, after Gd wash-out. The results, reported in FIG. 4, indicate a substantial (about 80%) and immediate loss of Gd from the cell bodies. The amount of Gd retained remains essentially constant up to four hours then declines again. This experiment was necessary to verify that in the neutron bombardment conditions the cells still retained Gd.

Neutron Irradiation:

To verify if the 140 $\mu$g/ml of Gd retained by glioblastoma cells in the two- to four-hour washout time was still available as an efficient tumoricidal agent for NCT, the cultures were irradiated for one hour with thermal neutrons. This experiment was performed in the absence of extracellular Gd, to demonstrate that the short range products of the Gd neutron capture reaction, i.e., the Auger electrons, and not the long range $\gamma$-rays, are responsible for double-stranded DNA damage and cell death.

Figure 5:
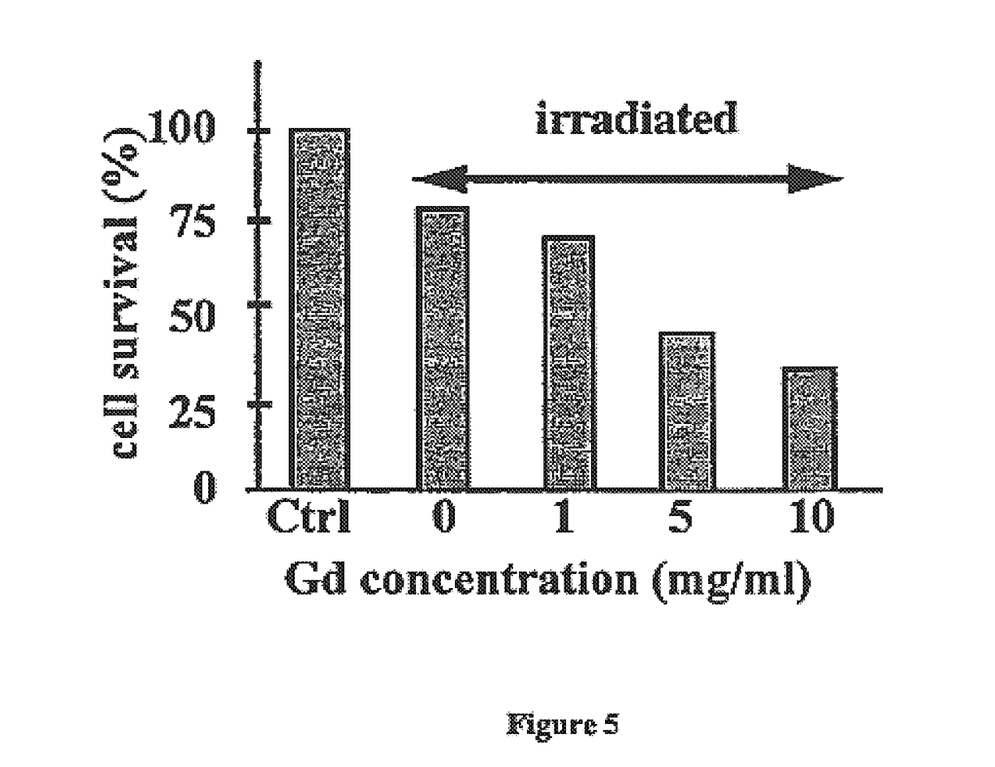
FIG. 5 is a graph depicting glioblastoma cell survival after neutron beam irradiation. The cell cultures were exposed to the indicated Gd-DTPA concentrations for 72 hours. The Gd-DTPA media were removed and replaced with a physiological solution two hours before the 1-hour irradiation. Two hours later the cells were detached from the plates and counted. Control cultures were grown in the absence of Gd. The cell survival numbers reported were obtained averaging the results on four series of cell cultures, with standard deviation within 10%.

As shown in of FIG. 5, the amount of Gd retained at the highest exposure concentrations employed (10 and 5 mg/ml), was enough to produce an evident and reproducible cell death on the four cell cultures (repeated twice, each time in duplicate). The Gd concentration retained by cells exposed to 1 mg/ml Gd-DTPA, in contrast, is not sufficient to induce consistent cell death.

The data of FIG. 5 were obtained by direct living cell count and very similar results were obtained by the use of an MTT assay. As presented in FIG. 5, the control cultures (no Gd) were also affected by neutron irradiation, causing 20% of the cells to die. It was found that the use of the physiological solution does not impair cell viability at least for 24 hours. The serum-free environment insures that the DNA-

TABLE 2

| | Detection Rate (Counts/s) for Individual Isotopes | | | | | | | |
|---|---|---|---|---|---|---|---|---|
| | $^{155}$Gd | $^{158}$Gd | $^{156}$Gd | $^{160}$Gd | $^{155}$GdO | $^{156}$GdO | $^{157}$GdO | $^{160}$GdO |
| Cell 1 | | | | | | | | |
| Nucleus | 12.98 | 1.03 | 1.36 | 1.72 | 1.35 | 1.59 | 1.85 | 2.23 | 1.88 |
| Cytoplasm | 6.44 | 0.41 | 0.89 | 0.91 | 0.68 | 0.63 | 0.91 | 2.08 | 0.94 |
| Ratio | 2.02 | 2.51 | 1.53 | 1.89 | 1.99 | 2.52 | 2.03 | 2.06 | 2.00 |
| Cell 2 | | | | | | | | |
| Nucleus | 5.13 | 0.37 | 0.59 | 0.69 | 0.54 | 0.51 | 0.72 | 0.89 | 0.86 |
| Cytoplasm | 3.21 | 0.23 | 0.32 | 0.37 | 0.33 | 0.38 | 0.51 | 0.57 | 0.5 |
| Ratio | 1.60 | 1.60 | 1.84 | 1.86 | 1.63 | 1.34 | 1.41 | 1.56 | 1.72 |

Table 2. TOF-SIMS analysis of two individual asked cells from the culture exposed to Gd-DTPA for 72 hours. The local gadolinium concentration was measured from 6 × 6 $\mu$m$^2$ areas on the nucleus or cytoplasm of each cell by recording the count rate of sputtered secondary gadolinium ions. The signal from all the naturally present Gd isotopes and oxides were recorded as shown, and added to give the total Gd ion yield displayed in the first data column on the left. For both cells, the nucleus:cytoplasm ratio of gadolinium ion yield exceeded 1.5:1.

Gadolinium Uptake vs. Exposure Concentration:

To verify whether the amount of Gd internalized by the glioblastoma cells was related to the Gd concentration in the repair cellular mechanism is slowed down, resulting (in principle) in decreased survival of the cells in which the Gd neutron capture reaction induced DNA damage. The 20% cell killing observed in cells not exposed to Gd provides an evaluation of the extent of this phenomenon.

Discussion of Examples:

The TOF-SIMS analysis of an un-ashed cell clearly demonstrates that Gd is internalized. Thus the ICP-MS and MEPHISTO measurements of Gd can be confidently interpreted as measurements of the internal concentration. Cell etching removed the carbon matrix and allowed a systematic study of intracellular localization with spectromicroscopy to provide statistical weight to the repeated observations of elevated gadolinium signals from nuclei relative to the surrounding cytoplasm. The MEPHISTO spectromicroscope is well suited for serial analyses of this kind.[13,19]

On a macroscopic scale, MRI routinely demonstrates that gadolinium compounds may be preferentially accumulated in tumor tissue in vivo. The degree of retention of Gd-DTPA by tumor has been correlated with the disruption of the blood brain barrier (BBB)[8,10] and this is consistent with the application of GdNCT to high grade gliomas in which BBB disruption is severe. The present results in vitro prove that Gd-DTPA can penetrate the membrane of cultured cells, and accumulate with an elevated concentration in cell nuclei. This finding is not shown in the prior art.

It is expected that this process will also occur from the extracellular space of tumors in mammalian patients and load the cancer cells with sufficient Gd for GdNCT to inhibit the growth of tumor cells. The exposure times used in the above in vitro experiments were long relative to the Gd-DTPA half life in the blood (around 30 minutes), therefore multiple or continuous extended administrations of the Gd compound is advisable. A cellular concentration of 250 µg/ml is generally recommended for GdNCT to be successful[4]. A maximum cellular concentration 2.4 times this value was achieved in the Examples after the 120-hour exposure (600 µg/ml) and more than 250 µg/ml after 24 hours. It was also found that the Gd concentration of 140 µg/ml still present in the cells after two hours in physiological solution was sufficient to induce death in 70% of the cells with thermal neutron bombardment. These values strongly suggest that reasonable quantities of Gd can be delivered to human tumors before the Gd-containing compound is removed from the blood.

Cell survival and continuous cell population increase after such long exposure times demonstrate no toxic effects of Gd-DTPA, hence multiple administrations of the drug to a patient to maximize tumor uptake, as considered for BNCT, will be tolerated.

The cell-killing effect of thermal neutron irradiation further demonstrates that Gd is accumulated intracellularly and that the concentration of Gd in the cells is sufficient to induce cell death, presumably through DNA damage.

In the Examples, the killing effect on cultured glioblastoma cells was about 20% after radiation alone and 70% after Gd exposure followed by thermal neutrons. This finding is consistent with a cell inactivation by Gd plus thermal neutrons that is 3.5 times more effective than thermal neutrons alone. Although $^{157}$Gd-enriched Gd-DTPA would be preferable for GdNCT (at a greater cost), the naturally-occurring Gd isotopic mixture was used in the Examples. Such mixture contains 15% $^{155}$Gd, having a cross section for thermal neutrons of 61,000 barn, and 15.7% $^{157}$Gd, having a cross section for thermal neutrons of 254,000 barn, the other isotopes having less than 2 barn. A natural Gd mixture has a weighted, effective cross section for thermal neutrons of $\{(15\times61{,}000+15.7\times254{,}000)/100\}=49{,}028$ barn, which is much greater than the other physiological elements present in tissue, and therefore useful for inducing selective cell killing with GdNCT.

It is reported that following irradiation with thermal neutrons, human glioma cells that have previously been exposed to boron compounds exhibit a cell inactivation which is 4.9 times more effective than neutrons alone[24]. It is worth noticing that the glioma cells seem less sensitive to BNCT as compared with human colon carcinoma cells, in which boron exposure followed by thermal neutrons results in 10.5 times more cell death than the thermal neutrons alone[26].

The killing effect of BNCT also depends on the preincubation time of cells in boron-containing culture medium[27]. The Examples demonstrate that Gd reaches the highest concentration in the glioblastoma cells after 120-hour exposure, and that this phenomenon is not related to a disruption of the cell membrane secondary to Gd toxicity because Ca distribution is not changed in these cells.

CONCLUSIONS

The much larger neutron capture cross section of the $^{157}$Gd isotope as compared to boron makes GdNCT a promising alternative boron NCT. The dose contribution of the GdNCT reaction from short range Auger electron emission has often been neglected because it was assumed that Gd-compounds remained extracellular and could not reach the cell nucleus. The Examples show, however, that Gd-DTPA not only penetrates the plasma membrane of the cell, but accumulates at higher concentration in the nucleus than in the cytoplasm.

The Examples also clearly prove that the nuclear Gd concentration is sufficient to induce cell death with thermal neutron irradiation in vitro. These results in vitro indicate that in vivo Gd-DTPA uptake in human glioblastoma patients can be used to inhibit the growth of the glioblastoma or to kill the glioblastoma cells selectively.

Bibliography

1. Chadha, M., Capala, J., Coderre, J. A., Elowitz, E. H., Iwai, J. I., Joel, D. D., Lui, H. B., Wielpolski, L., & Chanana, A. D (1998). Int. J. Radiation Oncology, Biol. Phys. 40, 829–834.
2. Hatanaka, H., & Nakagawa, Y. (1994) Int. J. Radiation Oncology, Biol. Phys. 28, 1061–1066.
3. Sauerwein, W., Moss, R., Rassow, J., Stecher-Rasmussen, F., Hideghety, K., Wolbers, J. G., & Sack, H. (1999) Strahlentharapie und Onkologie 175, 108–111.
4. Hill, J. S., Kahl, S. B., Stylli, S. S., Nakamura, Y., Koo, M., & Kaye, A. H. (1995) Proc. Natl. Acad. Sci. 92, 12126–12130.
5. Pak, R. H., Primus, F. J., Rickard-Dickson, K. J., Ng, L. L., Kane, R. R., & Hawthorne, M. F. (1995) Proc. Natl. Acad. Sci. 92, 6986–6990.
6. Nakanishi, A., Guan, L., Kane, R. R., Kasamatsu, H., & Hawthorne, M. F. (1999) Proc. Natl. Acad. Sci. 96, 238–241.
7. Young, S. W., Qing, F., Harriman, A., Sessler, J. L., Dow, W. C., Mody, T. D., Hemmi, G. W., Hao, Y., & Miller, R. A. (1996) Proc. Natl. Acad. Sci. 93, 6610–6615.
8. Shih, J. A., Brugger, R. M., (1992).in Progress in Neutron Capture Therapy, eds. Allen, B. J., Moore, D. E., & Harrington, B. V. (Plenum Press, New York), 183–186.
9. Rivard, M. J., Waid, D. S., & Wierzbicki, J. G., (1997) in Progress in Neutron Capture Therapy, eds. Larsson, B., Crawford, J., & Weinrich, R. (Elsevier, Amsterdam), 430–435.
10. Shih J.-L., & Brugger R. M. (1992) Med. Phys. 19, 733–744.
11. Niendorf, H. P., Felix, R., Laniado, M., Schorner, W., Kornmesser, W., & Claussen, C. (1986) Acta Radiol. Suppl. 369, 561–563.

12. Weinmann, H.-J., Brasch, R. C., Press, W.-R., & Wesbey, G. E. (1984) Am. J. Roentgenol. 142, 619–624.
13. Yoshida, K., Furuse, M., Kaneoke, Y., Saso, K., Inao, S., Motegi, Y., Ichihara, K., & Izawa, A. (1989) Mag. Reson. Imaging 7, 9–15.
14. Martin, R. F., D'Chuna, G., Pardee, M., & Allen, B. J. (1989) Pigment Cell Res. 2, 330–332.
15. Laster, B. H., Shani, G., Kahl, S. B., & Warkentien, L. (1996) Acta Oncol. 35, 917–923.
16. Hofmann, B., Fischer, C.-O., Lawaczeck, R., Platzek, J., & Semmler, W. (1999) Invest. Radiol. 34, 126–133.
17. De Stasio, G., Dunham, D., Tonner, B. P., Mercanti, D., Ciotti, M. T., Angelini, A., Coluzza, C., Perfetti, P. & Margaritondo, G. (1993) Neuroreport 4, 1175–8.
18. Gilbert, B., Perfetti, L., Fauchoux, O., Redondo, J., Baudat, P.-A., Andres, R., Neumann, M., Steen, S., Gabel, D., Mercanti, D., Ciotti, M. T., Perfetti, P., Margaritondo, G. and De Stasio G. Phys. Rev. E. in press.
19. Berger, B., Fischer, C. O., Lawaczeck, R., Platzek, J., Schwartz-Porsche, D. and Semmler, W. (1997) in Progress in Neutron Capture Therapy, eds. Larsson, B., Crawford, J., & Weinrich, R. (Elsevier, Amsterdam), 440–446.
20. De Stasio, G., Perfetti, L., Gilbert, B., Fauchoux, O., Capozi, M., Perfetti, P., Margaritondo, G., & Tonner, B. P. (1999) Rev. Sci. Instrum. 70, 1740–1742, and the references therein.
21. Kleihues, P., Burger, & P. C., Scheithauer, B. W. (1993) Brain Pathol. 3, 255–268.
22. De Stasio, G., Gilbert, B., Perfetti, L., Hansen, R., Mercanti, D., Ciotti, M. T., Andres, R., White, V. E., Perfetti, P., & Margaritondo, G. (1999) Anal. Biochem. 266, 174–180.
23. Gilbert, B., Perfetti, L., Hansen, R., Mercanti, D., Ciotti, M. T., Casalbore, P., Andres, R., Perfetti, P., Margaritondo, G. & De Stasio, G. (2000) Frontiers in Bioscience 5, 10–17.
24. http://www.bioscience.org/2000/v5/a/gilbert/fulltext.htm.
25. Kasrai, K., Bancroft, G. M. et al. (1996) Appl. Surf. Sci. 99, 303–309.
26. Ausserer, W. A., Ling, Y.-C., Chandra, S., & Morrison, G. H. (1989) Anal. Chem. 61, 2690–2695.
27. Li et al. (1999) J. Am. Chem. Soc. 121:1413–1414.

What is claimed is:

1. A method of inhibiting the growth of neoplastic cells, the method comprising:
   (a) contacting neoplastic cells with a Gd-containing compound for a time sufficient to allow the Gd-containing compound to be internalized within nuclei of the neoplastic cells; and then
   (b) exposing the neoplastic cells from step (a) to a thermal or epithermal neutron flux sufficient to induce a neutron capture reaction in Gd atoms within the Gd-containing compound internalized by the neoplastic cells, whereby growth of the neoplastic cells is inhibited due to cellular damage caused by Auger electrons and gamma radiation emitted by Gd atoms that underwent the neutron capture reaction.

2. The method of claim 1, wherein in step (a), the neoplastic cells are contacted with a Gd-containing compound wherein Gd atoms are present in naturally-occurring Gd isotopic ratio.

3. The method of claim 1, wherein in step (a), the neoplastic cells are contacted with a Gd-containing compound enriched in $^{157}$Gd.

4. The method of claim 1, wherein in step (a), the neoplastic cells are contacted with gadolinium diethylene triamine pentaacetic acid (Gd-DTPA) or a derivative thereof.

5. The method of claim 1, wherein in step (a), the neoplastic cells are contacted with $^{157}$Gd-enriched gadolinium diethylene triamine pentaacetic acid $^{157}$Gd-DTPA) or a derivative thereof.

6. The method of claim 1, wherein in step (a), the neoplastic cells are glioblastoma cells.

7. The method of claim 1, wherein in step (a), the neoplastic cells are human glioma cells.

8. The method of claim 1, wherein in step (a), the neoplastic cells are mammalian glioma cells within a mammalian subject suffering from glioma, and the cells are contacted with the Gd-containing compound by administering the Gd-containing compound to the mammalian subject.

9. The method of claim 8, wherein the mammalian subject is a human.

10. The method of claim 1, wherein in step (a), the Gd-containing compound is admixed with a pharmaceutically-acceptable carrier.

11. A method of treating glioma in mammalian subjects, comprising:
   (a) to a subject suffering from glioma, administering, intravenously or intracranially, an amount of a non-toxic, Gd-containing compound, the amount being sufficient to allow the compound to be internalized within nuclei of glioma cells within the subject; and then
   (b) exposing the glioma cells from step (a) to a thermal or epithermal neutron flux sufficient to induce a neutron capture reaction in Gd atoms within the Gd-containing compound internalized by the glioma cells, whereby growth of the glioma cells is inhibited due to cellular damage caused by Auger electrons and gamma radiation emitted by Gd atoms that underwent the neutron capture reaction.

12. The method of claim 11, wherein in step (a), a Gd-containing compound wherein Gd atoms are present in naturally-occurring Gd isotopic ratio is administered.

13. The method of claim 11, wherein in step (a), a Gd-containing compound enriched in $^{157}$Gd is administered.

14. The method of claim 11, wherein in step (a), gadolinium diethylene triamine pentaacetic acid (Gd-DTPA) or a derivative thereof is administered.

15. The method of claim 11, wherein in step (a), $^{157}$Gd-enriched gadolinium diethylene triamine pentaacetic acid ($^{157}$Gd-DTPA) or a derivative thereof is administered.

16. The method of claim 11, wherein in step (a), the Gd-containing compound is administered to a human subject.

17. The method of claim 11, wherein in step (a), the Gd-containing compound is admixed with a pharmaceutically-acceptable carrier prior to administering it to the subject.

18. A method of inhibiting the growth of neoplastic cells, the method comprising:
   (a) contacting neoplastic cells with a Gd-containing compound enriched in $^{155}$Gd for a time sufficient to allow the Gd-containing compound to be internalized within nuclei of the neoplastic cells; and then
   (b) exposing the neoplastic cells from step (a) to a thermal or epithermal neutron flux sufficient to induce a neutron capture reaction in Gd atoms within the Gd-containing compound internalized by the neoplastic cells, whereby growth of the neoplastic cells is inhibited due to cellular damage caused by Auger electrons and gamma radiation emitted by Gd atoms that underwent the neutron capture reaction.

19. The method of claim 18, wherein in step (a), the neoplastic cells are contacted with $^{155}$Gd-enriched gadolinium diethylene triamine pentaacetic acid ($^{155}$Gd-DTPA) or a derivative thereof.

20. A method of treating glioma in mammalian subjects, the method comprising:
   (a) to a subject suffering from glioma, administering, intravenously or intracranially, an amount of a non-toxic, Gd-containing compound enriched in $^{155}$Gd, the amount being sufficient to allow the compound to be internalized within nuclei of glioma cells within the subject; and then
   (b) exposing the glioma cells from step (a) to a thermal or epithermal neutron flux sufficient to induce a neutron capture reaction in Gd atoms within the Gd-containing compound internalized by the glioma cells, whereby growth of the glioma cells is inhibited due to cellular damage caused by Auger electrons and gamma radiation emitted by Gd atoms that underwent the neutron capture reaction.

21. The method of claim 20, wherein in step (a), $^{155}$Gd-enriched gadolinium diethylene triamine pentaacetic acid ($^{155}$Gd-DTPA) or a derivative thereof is administered.

22. A method of inhibiting the growth of neoplastic cells, the method comprising:
   (a) contacting neoplastic cells with Gd-DTPA for a time sufficient to allow the Gd-DTPA to be internalized within nuclei of the neoplastic cells; and then
   (b) exposing the neoplastic cells from step (a) to a thermal or epithermal neutron flux sufficient to induce a neutron capture reaction in Gd atoms within the Gd-DTPA internalized by the neoplastic cells, whereby growth of the neoplastic cells is inhibited due to cellular damage caused by Auger electrons and gamma radiation emitted by Gd atoms that underwent the neutron capture reaction.

23. The method of claim 22, wherein in step (a), $^{157}$Gd-enriched Gd-DTPA is administered.

* * * * *